United States Patent [19]
Ducheyne et al.

[11] Patent Number: 5,830,480
[45] Date of Patent: Nov. 3, 1998

[54] STABILIZATION OF SOL-GEL DERIVED SILICA-BASED GLASS

[75] Inventors: Paul Ducheyne, Rosemont, Pa.;
Shulamith Radin, Voorhees, N.J.;
Sylvie Falaize, Lyons, France; Erick Manuel Santos, San Antonio, Tex.

[73] Assignee: The Trustees of the University of Pennsylvania, Philadelphia, Pa.

[21] Appl. No.: 647,007

[22] Filed: May 9, 1996

[51] Int. Cl.$^6$ ................................................ A61K 9/00
[52] U.S. Cl. .................. 424/400; 424/421; 424/422; 424/484; 424/489; 424/490; 424/602; 424/724
[58] Field of Search ................................. 424/400, 408, 424/417, 421, 422, 484, 489, 490, 602, 724

[56] References Cited

U.S. PATENT DOCUMENTS

| | | | |
|---|---|---|---|
| 4,871,384 | 10/1989 | Kasuga | 65/30.1 |
| 5,002,890 | 3/1991 | Morrison | 435/286 |
| 5,068,122 | 11/1991 | Kokubo et al. | 427/2 |
| 5,204,106 | 4/1993 | Schepers et al. | 424/423 |
| 5,308,764 | 5/1994 | Goodwin et al. | 435/240.24 |
| 5,433,956 | 7/1995 | Patel | 424/400 |
| 5,480,844 | 1/1996 | Matsui et al. | 501/3 |
| 5,591,453 | 1/1997 | Ducheyne et al. | 424/484 |

OTHER PUBLICATIONS

Cornell et al., "Newest Factors in Fracture Healing", *Clin. Orthop.*, 1992, 227, 297–311.

Ducheyne, P., "Bioglass Coatings and Bioglass Composites as Implant Materials", *J. Biomed. Mat. Res.*, 1985, 19, 273–291.

Li et al., "Apatite Formation Induced by Silica–Gel in a Simulated Body–Fluid", *J. Amer. Ceram. Soc.*, 1992, 75, 2094–2097.

Nicoll et al., "A Novel Xerogel Carrier for Controlled Release of Biologically Active Molecules: III TGF–beta1", (Abstract), *Trans. Soc. Biomaterials*, 1995, 18, 290.

Norden, C.W., "Antibiotic Prophylaxis in Orthopedic Surgery," *Rev. Infec. Dis.*, 1991, 13 (Suppl 10), S842–846.

Pereira et al., "Calcium Phosphate Formation on Sol–Gel–Derived Bioactive Glasses in vitro", *J. Biomed. Mat. Res.*, 1994, 28, 693–698.

Radin et al., "A Novel Xerogel Carrier for Controlled Release of Biologically Active Molecules: I Antibiotics (Vancomycin)", (Abstract), *Trans. Soc. Biomaterials*, 1995, 18, 289.

"In Vitro Release of Transforming Growth Factor Beta–1 from a Xerogel Carrier", Chapter 6, pp. 121–145.

"In Vitro Cell Bioassay Using Stromal Marrow Cells to Evaluate Si–Ca–P Xerogels with Incorporated Bone Morphogenetic Protein", Chapter 7, pp. 146–162.

*Primary Examiner*—Neil S. Levy
*Attorney, Agent, or Firm*—Woodcock Washburn Kurtz Mackiewicz & Norris LLP

[57] ABSTRACT

Methods for increasing the biocompatibility of silica-based glass having a concentration of silicon greater than 55%, compositions resulting therefrom, and methods for expeditious formation of calcium-phosphate films on sol-gel derived, silica-based bioactive glass are disclosed.

19 Claims, 3 Drawing Sheets

STABILIZATION OF SOL-GEL DERIVED SILICA-BASED GLASS

GOVERNMENT RIGHTS

The United States government may have rights to certain aspects of this invention.

FIELD OF THE INVENTION

This invention relates to the treatment of sol-gel derived silica-based glass to increase biocompatibility.

BACKGROUND OF THE INVENTION

The treatment of musculoskeletal conditions such as open and non-union fractures, and loosened prostheses with extensive bone loss involves prophylactic and therapeutic use of antibiotics and analgesics. The local delivery of these drugs has the dual advantage of decreasing the risks of systemic toxicity and side effect associated with oral and parenteral therapies, while also improving the efficacy of the treatment by achieving higher drug concentrations in the desired tissues. Norden CW., "Antibiotic Prophylaxis in Orthopedic Surgery," *Rev. Infect. Dis.*, 13 (Suppl 10):S842–6, 1991. The recent identification of growth factors capable of affecting bone cell function has created new avenues for the treatment of orthopaedic conditions. Cornell et al., "Newest factors in fracture healing," *Clin. Orthop.*, 277:297–311, 1992. Delivered appropriately to the site of interest, these factors may facilitate bone tissue healing.

There is a need for materials capable of releasing biologically active molecules at bone sites to affect growth, combat infection, and/ or control pain. The ideal delivery vehicle should release biomolecules in a controlled manner and for time spans long enough to provide optimum effectiveness of the drug. Additionally, when extensive bone regeneration is needed, a biomolecule carrier that could also serve as a scaffold for bone tissue growth would be beneficial. Hence bioactive materials, i.e. materials able to bond to bone, are of interest for such an application.

Sol-gel derived glasses are very promising controlled release materials for use in bone therapies, as they are able to release functional biomolecules in a controlled fashion. Radin et al., "A Novel Xerogel Carrier for Controlled Release of Biologically Active Molecules: I Antibiotics (Vancomycin)," [Abstract] *Trans. Soc. Biomaterials*, 18:289, 1995; and Nicoll et al., "A Novel Xerogel Carrier for Controlled Release of Biologically Active Molecules: III TGF-beta1," [Abstract] *Trans. Soc. Biomaterials*, 18:290, 1995. In addition, it has been shown that they form a Ca—P layer in vitro. These novel materials are room-temperature prepared, silica-based and amorphous, and have a high ultramicroscopic porosity.

Sol-gel derived processing can be performed at low temperatures—i.e. approximately 40° C. or below—and low pH. Both of these conditions can be important for uniformly incorporating the biologically active molecules and for maintaining the functionality of biologically active molecules incorporated into the sol-gel matrix. The advantages of sol-gel derived processing include the following: 1) a sol, which is a suspension of colloidal size particles, is in liquid form before it gels; 2) the whole reaction can be done at room temperature; and 3) the microporosity of sol-gel glasses can be controlled by, for example, varying water content, timing of proton addition, proton concentration, aging time, and drying time. The pore sizes achievable with sol-gel processing in general are in the nanometer range.

During the liquid phase of the reaction, proteins and other biologically active molecules can be added to the liquid sol before it gels. These molecules then become encased in the solid matrix. A controlled release of these molecules is achieved upon subsequent immersion or implantation.

In vivo studies with implanted sol-gel derived, silica-based glass revealed, however, that the glass can be very reactive, in part due to its dissolution properties, and can cause inflammatory reactions. Granules of four types of sol-gel derived glasses, processed at room temperature, were implanted for either 2 or 4 weeks in 5 mm diameter and 2.5 mm deep defects created in the rabbit iliac crest. Three of the materials comprised 100% $SiO_2$ (S100) and one of them contained (W,%) 70% $SiO_2$—25%CaO—5%$P_2O_5$ (S70) . One of the S100 materials further contained 1.2 mg of Vancomycin per gram of material (S100V) . All the materials were tested as 500–710 $\mu$m granules.

Histological analysis of the retrieved samples at the end of the implantation periods revealed a significant degradation, i.e., a significant decrease in size, of the implanted sol-gel granules. As is typical for most material resorption, the degradation resulted in an inflammatory response, as indicated by the presence of phagocytozing cells around and in between the granules. The degree of degradation and inflammatory response was significantly greater for the S70 material. A better control of the degradation rate is warranted to minimize the inflammatory response upon implantation.

The findings of the in vivo studies paralleled what had been observed in vitro. When dissolution experiments were performed in vitro, using frequent solution exchange to model the non-equilibrium in vivo conditions, a fast dissolution of silicon was observed, with the rate of dissolution being faster for S70 than for S100 glass.

Although the presence of vancomycin in the compositions reduced the inflammatory response, a means for stabilizing the glass compositions for greater control of in vivo activity is needed.

SUMMARY OF THE INVENTION

In one aspect, the invention relates to sol-gel derived, silica-based glass compositions which have been treated to reduce dissolution of silicon upon contact with physiological solutions. The compositions comprise a silicon-containing glass material surrounded by a calcium-phosphate surface layer.

In another aspect, the invention relates to a method for stabilizing sol-gel derived silica-based glass compositions by immersing in a solution saturated in silicon. This leads to reduced silicon dissolution rates upon subsequent contact with physiological solutions.

In a further aspect, the invention relates to a method for treating sol-gel derived, silica-based glass to form a calcium-phosphate surface layer by immersing in a solution which is initially silicon-free and which provokes rapid dissolution of silicon, representing less than 1% loss of the sol-gel by weight, into the solution, thereby achieving silicon saturation.

DETAILED DESCRIPTION OF THE INVENTION

Figure 1A:
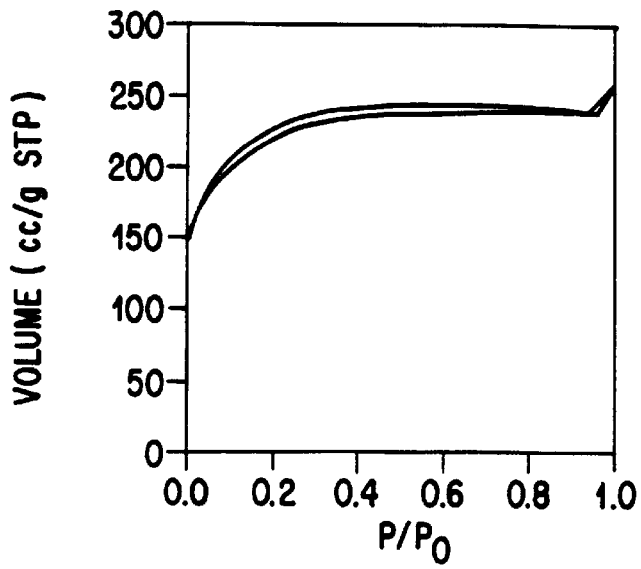
FIGS. 1*a–c* depict isotherms (plots of volume of absorbate to partial pressure) obtained for S100, S100V and S70, respectively.

This invention involves a method for treating sol-gel derived, silica-based glass, and the compositions resulting therefrom, so that a calcium phosphate film is formed on the glass surface. The calcium-phosphate film is formed without extensive degradation of the glass. The calcium-phosphate film can also comprise biologically active molecules.

Previous studies have shown that heat-treated sol-gel derived glasses in the system $SiO_2$, CaO and $P_2O_5$ (Pereira et al., "Calcium phosphate formation on sol-gel-derived bioactive glasses in vitro," *J. Biomed. Mat. Res.,* 28:693–8, 1994) as well as pure silica gels (Li et al., "Apatite Formation Induced by Silica-Gel in a Simulated Body-Fluid," *J. Amer. Ceram. Soc.* 75:2094–7, 1992) are able to induce apatite formation when immersed in simulated physiologic solutions. Room-temperature prepared sol-gels can also induce apatite formation in $Ca^{2+}$ and $PO_4^{2-}$ containing solutions. See, for example, U.S. Pat. application Ser. No. 08/477,585.

According to the present invention, sol-gel derived, silica-based glass can be treated to form a calcium-phosphate surface layer without extensive degradation of the glass by immersing the glass in calcium- and phosphate-containing solutions saturated in silicon. As discussed below, such glasses can be prepared with biologically active molecules incorporated in the matrix. Since degradation leads to a loss of incorporated molecules, preventing or minimizing degradation leads to a better retention of the biologically active molecules. This improves the overall yield of a production process intended to incorporate biologically molecules in controlled release, biocompatible carriers. Another aspect of the treatment is that the acid catalyzed sol-gel derived glass undergoes a restructuring on a molecular level due to dissolution—precipitation reactions which imparts greater stability to the glass.

It is also contemplated that the method can be applied to similar compositions from melt-derived bioactive glass having compositions other than those near that of the 45S5 glass, i.e., compositions containing concentrations of silicon of from about 55 to about 65% to create a calcium-phosphate surface layer. Other compounds, and oxides, may also be present, such as described in P. Ducheyne, "Bioglass coatings and bioglass composites as implant materials," *J. Biomed. Mat. Res.,* 19:273–291, 1985, incorporated herein by reference.

The sol-gel derived glass can be prepared following, for example, the procedures disclosed in U.S. application Ser. No. 08/477,585, hereby incorporated by reference. The compositional range for the sol-gel derived glass is as follows (in weight percent): $SiO_2$- 60–100; CaO - 3–30; and $P_2O_5$- 0–10.

As used herein, "without extensive degradation of the glass" refers to a loss of silicon of less than about 10%.

As used herein, the term "about" means approximately ±10% of the value modified.

As used herein, "silica-based" refers to the inclusion of a silicon oxide in the composition of the glass. Other oxides may also be present.

The invention includes immersion of the sol-gel glasses, either with or without incorporated bioactive molecules, in a Ca, P and Si-containing solution to form a surface Ca,P-layer due to solution-induced physico-chemical reactions. In order to prevent silica network dissolution during the immersion, Si content in the solution must be equal to or greater than the silicon solubility of the treatment solution in which silica-based material on which the CaP-layer to be formed is immersed. During the treatment, remaining by-products of sol-gel synthesis, such as alcohol, can also be released.

The reactions involved in the CaP-layer formation upon immersion in the Ca-,P-, and Si-containing solution are believed to be the following:

1) in the case of 100% SiO2 sol-gel glass, the layer formation occurs due to complexation of Ca and P-ions, present in the solution, with the surface silanols (SiOH); and 2) in the case of CaP-containing sol-gel glass, a diffusion of Ca ions from the material to the solution leads to an increase in the solution supersaturation with respect to CaP-phases and subsequent precipitation of the phases on the glass surface.

The treatment conditions (W/V ratio, solution composition and H, temperature, extent of immersion, etc.) are not restricted by the specific examples detailed below and, rather, can vary to a large degree. As will be readily apparent to one skilled in the art, the various conditions are interrelated and can be adjusted accordingly to achieve the present invention. The parameters for S100 glasses can vary, at least, as follows: pH—from about 6 to about 9; immersion time—up to about 10 days; Ca content—from about 2 to about 15 mM; total $PO_4$ (including $HPO_4$ and $H_2PO_4$) from about 1 to about 20 mM; other ions can also be present in the solution and include, without being limited thereto, Na, K, Cl, Mg, $CO_3$, and $SO_4$, and combinations thereof. For CaP-containing sol-gel glasses, for instance, containing 10% by weight of calcium oxide, the parameters can vary at least as follows: pH—from about 6 to about 9; immersion time—up to about 3 days; Ca content (in solution)—from about 0.5 to about 5 mM; total $PO_4$ content (in solution) from about 1 to about 20 mM; other ions can also be present in solution and include, without being limited thereto, Na, K, Cl, Mg, $SO_4$, and $CO_3$, and combinations thereof. The solutions used can be buffered by any suitable buffer including, but not limited to, tris buffer and phosphate buffer.

It has also been found that a calcium-phosphate surface layer can be formed on materials comprising sol-gel derived, silica-based glass by immersion in a solution which is initially silicon-free and which provokes rapid dissolution of silicon, representing less than 1% loss of the sol-gel by weight, into the solution, thereby achieving silicon saturation. For example, under the conditions detailed below in Example 3 below, a calcium-phosphate film was formed within three hours.

The glass materials to be treated can be in the shape of granules, disks, rods, or blocks of various sizes. Alternatively, the glass material to be treated may be in the form of a coating upon another material.

The sol-gel derived, silica-based glasses, with and without calcium oxide, can be prepared following, for example, the procedures disclosed in U.S. application Ser. No. 08/477, 585, hereby incorporated by reference. Both calcium alkoxides and calcium salts can be used as the calcium oxide source. Of course, other sol-gel procedures can also be used for preparing the silica-based glasses.

The treatment can be performed in solutions containing various biologically active molecules to produce protective coatings with the biologically active molecules incorporated therein to enhance the process of healing and repair. The biologically active molecules can be present during the treatment, or can be adsorbed subsequently such as by immersion in, for example, tissue culture medium containing serum, or any other physiological medium with the relevant molecules in solution. Alternatively, sol-gel derived bioactive glass can be prepared having the biologically active molecules incorporated in the matrix of the glass using the procedure as disclosed in application Ser. No. 08/477,585, discussed above.

As used herein, "biologically active molecules" are defined as those organic molecules having an effect in a biological system, whether such system is in vitro, in vivo, or in situ. Biologically active molecules include, but are not limited to, the following categories: growth factors, cytokines, antibiotics, anti-inflammatory agents, analgesics and other drugs, and cell attachment molecules.

The term "antibiotic" includes bactericidal, fungicidal, and infection-preventing drugs which are substantially water-soluble such as, for example, gentamicin, vancomycin, penicillin, and cephalosporins.

The term "growth factors" refers, without limitation, to factors affecting the function of cells such as osteogenic cells, fibroblasts, neural cells, endothelial cells, epithelial cells, keratinocytes, chondrocytes, myocytes, cells from joint ligaments, and cells from the nucleus pulposis. Platelet derived growth factors (PDGF), the transforming growth factors (TGF-$\beta$), insulin-like growth factors (IGFs), fibroblast growth factors (FGFs), and the bone morphogenetic proteins (BMPs) are examples of growth factors encompassed in the particles according to the present invention.

The term "cell attachment molecules" as used herein includes, but is not limited to, fibronectin, vitronectin, collagen type I, osteopontin, bone sialoprotein thrombospondin, and fibrinogen. Such molecules are important in the attachment of anchorage-dependent cells.

The term "contact" as used herein includes, but is not limited to, contact by immersion, implantation, and embedding.

EXAMPLE 1

Preparation of Sol-Gels

Three types of sol-gel derived particles were synthesized: 100% silica (S100), Vancomycin-silica composites (S100V), and calcium and phosphorus containing silica (S70). S100V contained 1.2 mg of Vancomycin per gram. S70 was composed of: 70% $SiO_2$, 25% CaO and 5% $P_2O_5$ (% by weight).

The alkoxides tetramethyl orthosilicate (TMOS—Aldrich Chemical Inc., Milwaukee Wis.), calcium methoxyethoxide (CME—Gelest Inc.,Tullytown Pa.) and triethyl phosphate (TEP—Strem Chemical Inc., Newburyport Mass.) were used as silicon, calcium and phosphorus sources respectively.

S100 and S100V were prepared from a mixture of TMOS and deionized (DI) water in a 1:10 molar ratio. The following procedure was used. Predetermined amounts of TMOS and deionized water, to maintain the molar ratio for the volume prepared, poured into a beaker which was immediately placed in an ice-cooled ultrasonic bath. For the Vancomycin-containing sol-gel, the amount of water added at this point precludes the amount of water to be added later with the antibiotic. Sonification was performed in the absence of solvent to prevent phase separation. Since sonification provides energy, ice cooling was used to prevent overheating. A small volume of acid catalyst (1N HCl) was then added. Within a few minutes, the mixture became homogenous. Ultrasonic stirring was continued for 20 to 25 minutes and the pH of the solution was measured. The pH did not exceed 3. While the sol was still being stirred and cooled, a previously prepared solution of Vancomycin (Vancoled—Lederle Parentals Inc., Carolina and Puerto Rico) in DI water was added when necessary. The solution was stirred for another five minutes. The sols were cast into preweighed polystyrene vials using a volumetric pipette. Three milliliters were dispensed into each vial. Next, the vials were weighed, sealed, and set aside to allow gelation to occur. The time to gelation was approximately 15 hours.

The gels were left to age for 3 days, with the vials remaining sealed. Afterwards, the gels were exposed to ambient air and dried to 70% loss of as-cast weight. The disks obtained were then crushed with a ceramic mortar and pestle, and sieved in a sonic sifter to produce particles of two diameter ranges: 210–500 micrometers and 500–710 micrometers. The resulting particles were stored in sealed polystyrene containers at 4° C.

The calcium and phosphorus containing sols were prepared in a glove box under an argon atmosphere. The following procedure was used. Prorated amounts of TMOS, CME, and TEP to arrive at s sol-gel composition having a final composition of 70% $SiO_2$, 25% CaO and 5% $P_2O_5$ (% by weight), were successively poured in a beaker. The mixture was magnetically stirred for about 5 minutes. The sol was cast into preweighed polystyrene vials, 2.23 ml per vial. After casting, the samples were removed from the glove box. To delay gelation, methanol was added in a 1:1 molar ratio with TMOS. The samples were vortexed immediately thereafter. Next, 0.1N acetic acid was added to each sample to simulate the addition of biologically active molecules dissolved in an acidic solution. Gelation occurred within a minute. The remainder of the procedure was the same as for the silica sol-gels.

EXAMPLE 2

Surface Layer Formation in Solution Supplemented with Silicon

S100 and S70 particles of diameter ranging from 500–710 micrometers were treated to develop a Ca—P film at their surface. The specimens were immersed in TE (a tris buffered solution with electrolyte content similar to that of human plasma, pH=7.4 at 37° C.) supplemented with 2.5 mM silicon (pH=7.6 at 37° C.) for 5 (S100) and 2 (S70) days. This concentration of silicon corresponds to the solubility of silicon in TE at pH 7.4 with the sol-gel immersed. The conditioning was performed with a weight of material to solution volume ratio of 0.5 mg/ml and the solution was continuously shaken. By measuring the calcium and phosphorus concentrations in solution, the surface precipitation reaction was continuously monitored. Upon expiration of the immersion times, the particles were collected and dried at room temperature under an air stream.

EXAMPLE 3

Synthesis; Surface Layer Formation in a Solution Initially Silicon-free

Silica-based, sol-gel discs with a composition (in percent by weight) of 70% $SiO_2$—25% CaO—5% $P_2O_5$ (S70) were synthesized utilizing three alkoxides—tetramethylorthosilane (TMOS), calcium methoxyethoxide (CME) and triethylphosphate(TEP). Specifically, 3.46 ml of TMOS, 0.24 ml of TEP and 8.4 ml of CME were mixed by magnetic stirring in a 30 ml beaker under an argon atmosphere. After 5 minutes the mixture was aliquoted into polystyrene containers in samples of 0.74 ml to which 0.26 ml protein solution was added. The protein solution consisted of 0.26 ml of 0.1N acetic acid and 1% bovine serum albumin (BSA). The resulting gels were aged (sealed) for 7 days at room temperature and dried to 50% of their original weight to obtain discs. The drying was carried out at room temperature and was carefully monitored to avoid cracking of the discs obtained. The discs were approximately 10 mm in diameter and 4 mm in height, giving a surface area of 1.257 $cm^2$. To prepare particles, discs were crushed using a mortar and pestle and sieved to a particle diameter range of 210–710 $\mu$m.

Discs and particles were pre-treated by immersion in sterile Dulbecco's phosphate-buffered saline (DPBS) (GibcoBRL/Life Technologies, Grand Island, N.Y.) for 3 hours at 37° C. in sterilized polystyrene sealed containers. For discs, a surface area to solution volume ratio of 0.1 $cm^{-1}$ was used; thus for a surface area of 1.257 $cm^2$, 12.57 ml of DPBS was used. Particles were immersed at a 1 mg/ml weight to solution volume ratio. DPBS has the following formulation of components per liter of solution (final pH of 7.4@37° C.): 0.10 g of $CaCl_2$ (anh.), 0.20 g of KCl, 0.20 g of $KH_2PO_4$, 0.10 g of $MgCl_2(6H_2O)$, 0.80g of NaCl, 1.15 g of $Na_2HPO_4$, 2.16 g of $Na_2HPO_4(7H_2O)$. P—O bend peaks were observed for immersed samples using Fourier transform infrared spectroscopy (FTIR) (Nicolet 5DXC) indicative of calcium phosphate layer formation.

EXAMPLE 4

Material Characterization

The particles disclosed in Example 2 were characterized by gas sorption (Quantachrome Autosorbl) and Fourier Transform Infrared Spectroscopy (FTIR, Nicolet 5DXC) after synthesis and after conditioning.

Figure 1B:
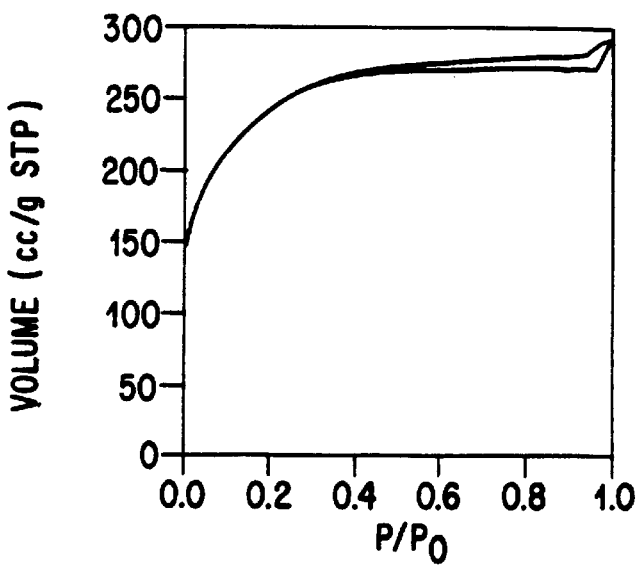
Figure 1C:
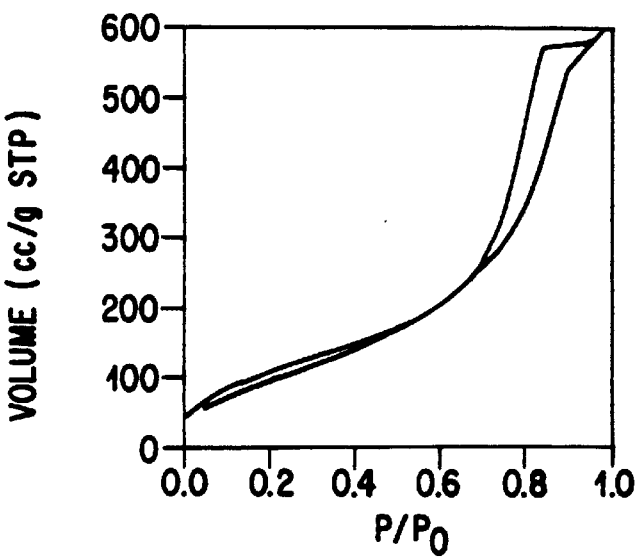

The isotherms (plots of volume of absorbate to partial pressure) obtained for S100, S100V and S70 are given in FIGS. 1a–c. The shape of the isotherms indicates that S100 is microporous (pore radius<20 Å) whereas S70 is mesoporous (20 Å<pore radius<500 Å). The type of hysteresis suggests a cylindrical pore geometry for both compositions. The addition of Vancomycin to S100 does not significantly affect the ultrastructure of the composite as indicated by a similar isotherm shape.

For all materials, the multi-point BET surface area, total pore volume, and mean pore radius were determined from the isotherms. The data are listed in Table I. S70 exhibits a smaller surface area and a larger pore size than S100 and S100V, as was deduced from the isotherms shape. The conditioning step considerably decreases the specific surface area and increases the pore size for both S100 and S70. Upon conditioning, the former acquires the characteristics of a mesoporous material. Furthermore the pore size of the treated S100 and S70 has a double-peaked distribution, suggesting the appearance of a second phase. This additional peak is of small intensity and located around 20 Å. Hence it can be distinguished more easily in the case of S70, whose mean pore size is about 100 Å. Additional experiments enable to assign this peak to the newly formed Ca—P phase.

TABLE I

| | Ultrastructural properties | | | | |
|---|---|---|---|---|---|
| | S100 | S100V | S70 | Cond. S100 | Cond. S70 |
| BET SSA ($m^2$/g) | 842 | 896 | 384 | 282 | 298 |
| Pore volume ($10^{-3} \cdot$ cc/g) | 410 | 465 | 949 | 440 | 454 |
| Mean pore radius (Å) | 10 | 10 | 50 | 31 20 | 98 20 |
| Structure | microporous | | mesoporous | | |

Figure 2A:
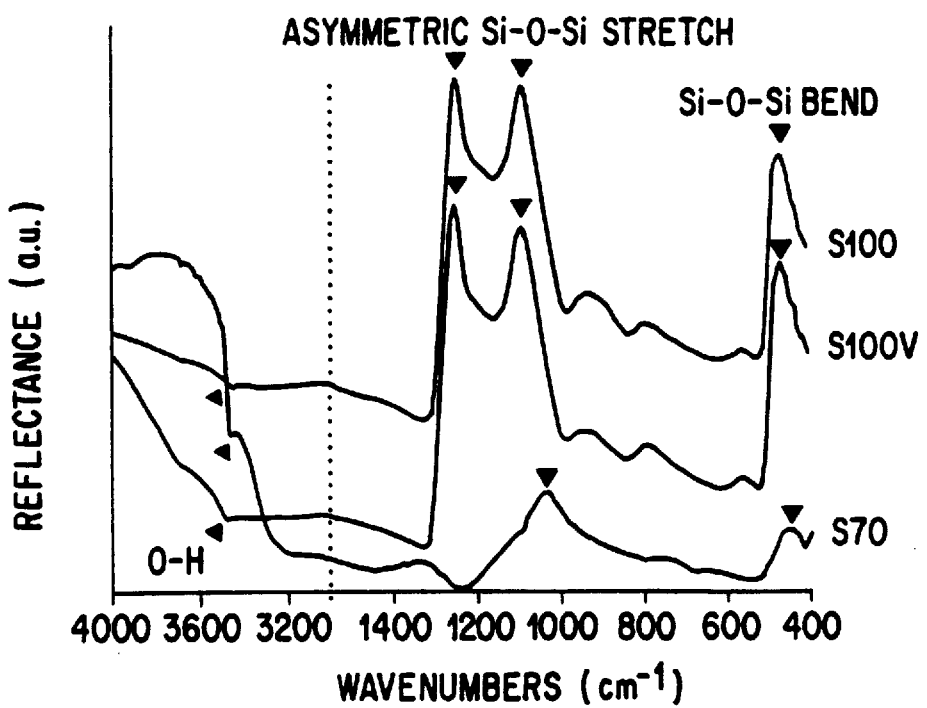
FIGS. 2*a* and *b* depict FTIR spectra obtained for each material prior to and after, respectively, treatment in solutions saturated with silicon.

FTIR spectra obtained for each material prior to treatment are shown in FIG. 2a. The major features associated with network vibrational modes of S100 are the 465, 787, 1088 and 1246 $cm^{-1}$ bands. The doublet formed by the 1088 and 1246 $cm^{-1}$ bands is assigned to Si—O—Si asymmetric stretching. The 787 $cm^{-1}$ vibration is associated with symmetric Si—O—Si stretching. Lastly, the 465 $cm^{-1}$ vibration is assigned to Si—O—Si bending mode. Two additional bands can be observed at 561 and 937 $cm^{-1}$. They are very likely the result of Si—O—Si bending in four-membered ring structures, and Si—OH stretching respectively. Incorporation of Vancomycin does not modify the appearance and location of these bands. The sharpness of the peaks associated with the main vibrational modes is typical for well polymerized silica. Moreover the absence of band in the 2800–3000 $cm^{-1}$ region, which could result from C—H stretching in remaining methoxy groups, indicates that these groups are completely hydrolyzed. For S70, the bands associated with asymmetric stretching and bending are broader and shifted to lower wavenumbers than for S100:from 1088 to 1038 $cm^{-1}$ and from 465 to 452 $cm^{-1}$ respectively. The bands associated with hydroxyl bonds in silanol groups can be observed at 3740 $cm^{-1}$ for S100 and 3695 $cm^{-1}$ for S70.

Figure 2B:
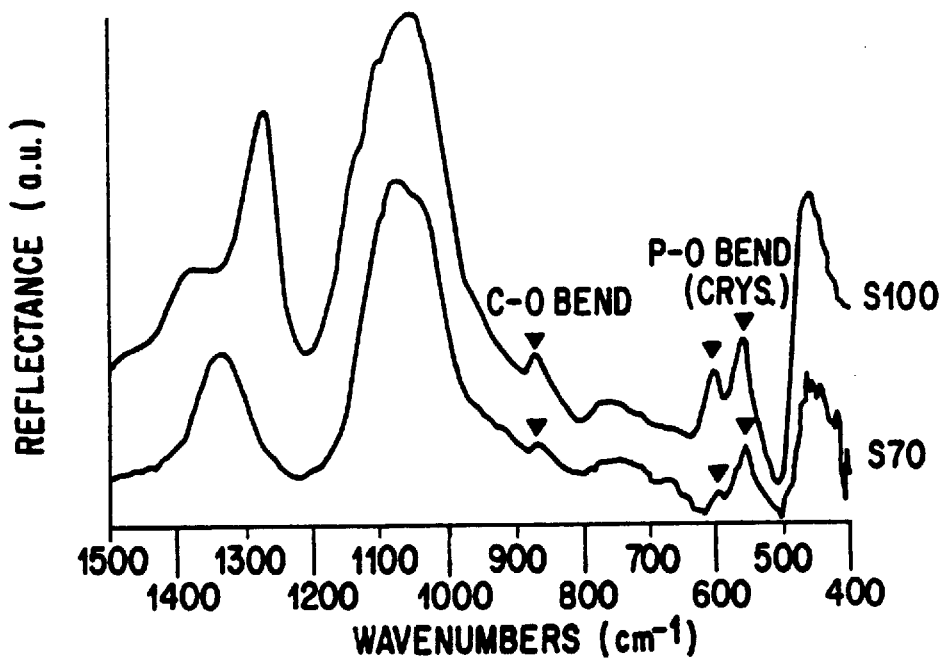

FTIR spectra of the S100 and S70 materials after treatment are depicted in FIG. 2b. The appearance of two peaks characteristic of P—O bending vibrations, at 560 $cm^{-1}$ and 604 $cm^{-1}$, indicates that a crystalline Ca—P phase has formed on the surface of both xerogels. C—O bending vibration at 870 $cm^{-1}$, which is characteristic of carbonate groups in carbonated hydroxyapatite (c—HA), is also detected for both conditioned xerogels. Thus the newly formed phase is carbonated hydroxyapatite.

EXAMPLE 5

In Vitro Dissolution Modelling Experiment

S100 and S70 treated according to Example 2 above, and untreated S100 and S70, were immersed in vitro in a simulated physiological solution, i.e., TE. Immersions were performed in vials at 37° C. TE is a non-proteinaceous solution that contains the electrolyte constituents of human blood plasma in similar concentrations (cf. Table II). TE was prepared by dissolving reagent grade NaCl, KCl, $NaHCO_3$, $MgCl_2.6H_2O$, $MgSO_4.7H_2O$, $KHPO_4$anh. and $CaCl_2.2H_2O$ in a 0.05M Tris [hydroxymethyl] aminomethane hydrochloride buffered solution. The resulting pH was 7.4 at 37° C.

TABLE II

Ionic content of human blood plasma and TE.

| Ion | Human blood plasma (mM) | TE (mM) |
|---|---|---|
| $Ca^{2+}$ | 2.5 | 2.5 |
| $HPO_4^{2-}$ | 1.0 | 1.0 |
| $Na^+$ | 142.0 | 152.0 |
| $Cl^-$ | 103.0 | 136.0 |
| $K^+$ | 5.0 | 5.0 |
| $Mg^{2+}$ | 1.5 | 1.5 |
| $HCO_3^-$ | 27.0 | 27.0 |
| $SO_4^{2-}$ | 0.5 | 0.5 |

A differential immersion was effected by exchange with fresh solution at various time points throughout the duration of immersion. In the present example, the samples were exposed to fresh solution after 3, 6, 9, 24, 48, 72, 96, 124 and 168 hours of immersion. These intervals were chosen in an attempt to maintain a maximum concentration of Si in solution less than ⅔ of the saturation concentration. The immersion protocol was intended to reflect the continuous replenishment of body fluid at the implant site. The samples were immersed for up to 7 days.

Three samples were tested. The weight to solution volume ratio was 0.5 mg/ml. The samples were placed in an incubator at 37° C. in a 5% $CO_2$ atmosphere and continuously shaken (200 revolutions/minute). The vials were loosely capped to minimize evaporation without preventing gas exchange. Upon completion of immersion, the solutions were collected and the retrieved particles were rinsed with ethanol and dried in ambient air. The Si concentrations were measured by flame atomic absorption spectrophotometry (FAAS, Perkin-Elmer 5100PC).

Figure 3A:
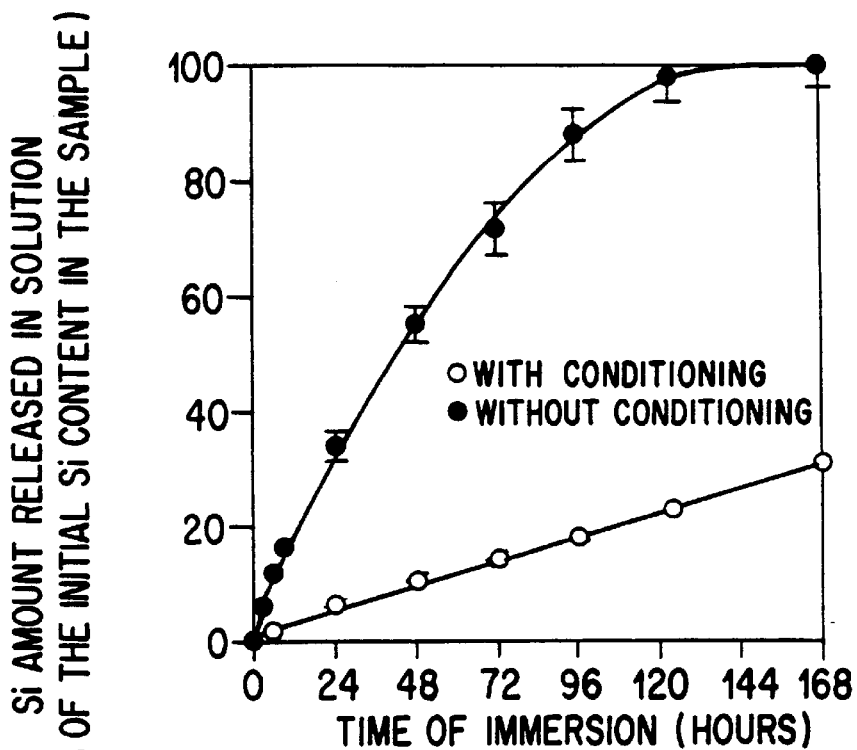
FIGS. 3a and b depict the effect of a preformed carbonated hydroxyapatite c—HA layer on the dissolution of S100 and S70 particles, respectively.
Figure 3B:
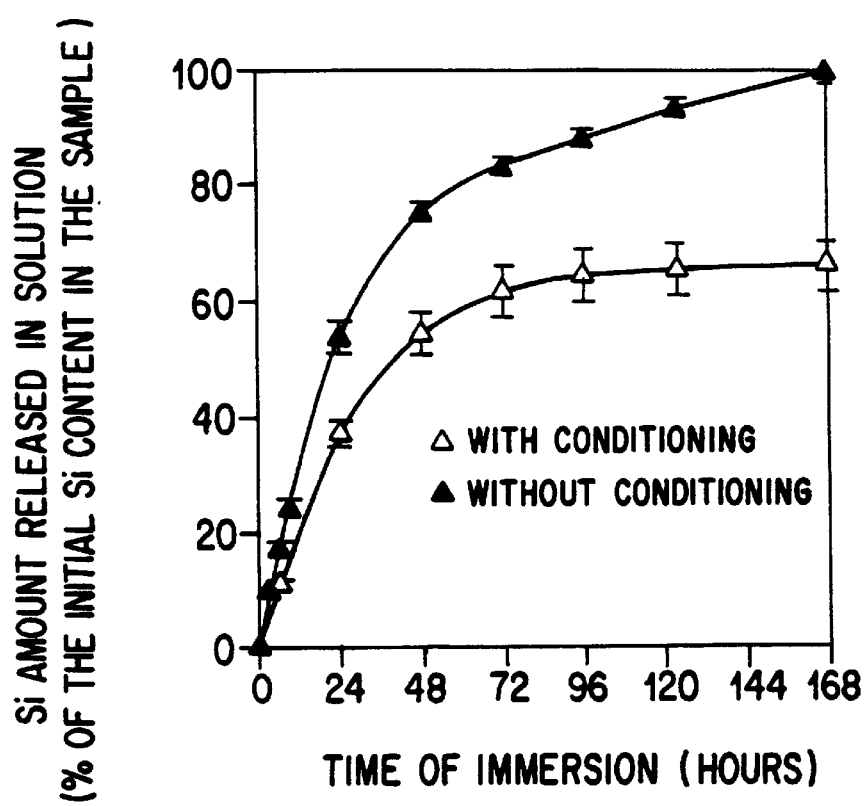

The effect of a preformed c—HA layer on the dissolution of S100 and S70 particles is shown in FIGS. 3a and b. For both samples, the conditioning step significantly decreased the rate and amount of Si dissolution. The reductive effect is much greater for S100. The Si release from the treated S100 follows a first order relationship with time with a correlation coefficient of 0.998.

The foregoing examples are meant to illustrate the invention and not to limit it in any way. Those skilled in the art will recognize that modifications can be made which are within the spirit and scope of the invention as set forth in the appended claims.

What is claimed is:

1. A material prepared by immersing a silica-based, glass composition having a silica concentration of from about 55 to about 100% in a solution saturated in silicon for a time sufficient to form a calcium-phosphate outer layer on said material without extensive degradation of said glass.

2. The composition of claim 1 wherein the silica-based glass is sol-gel derived.

3. The composition of claim 1 wherein the silica-based glass further comprises calcium and phosphate.

4. The composition of claim 2 wherein said glass further comprises biologically active molecules.

5. A method for increasing the biocompatibility of a silica-based, glass composition having a silica concentration of from about 55 to about 100% comprising immersing said glass in a solution saturated in silicon for a time sufficient to form a calcium-phosphate outer layer on said glass without extensive degradation.

6. The method of claim 5 wherein the silica-based glass is sol-gel derived.

7. The method of claim 5 wherein the silica-based glass further comprises calcium and phosphate.

8. The method of claim 5 wherein said solution further comprises biologically active molecules.

9. The method of claim 8 wherein said biologically active molecules comprise an antibiotic.

10. The method of claim 8 wherein said biologically active molecules comprise cell attachment molecules.

11. The method of claim 8 wherein said biologically active molecules comprise growth factors.

12. A method for treating silica-based glass having a silica concentration of from about 55 to about 100% to form an outer layer comprising calcium and phosphate, comprising immersing said glass in a solution which does not contain silicon initially, but which induces dissolution of silicon from said glass, whereby silicon saturation of said solution is achieved with a loss of silicon from said glass of 1 % by weight, or less, for a time sufficient to allow said calcium and phosphate outer layer to form.

13. The method of claim 12 wherein said solution is phosphate-buffered saline.

14. The method of claim 12 wherein the silica-based glass is sol-gel derived.

15. The method of claim 12 wherein the silica-based glass further comprises calcium and phosphate.

16. The method of claim 12 wherein said solution further comprises biologically active molecules.

17. The method of claim 16 wherein said biologically active molecules comprise a antibiotic.

18. The method of claim 16 wherein said biologically active molecules comprise cell attachment molecules.

19. The method of claim 16 wherein said biologically active molecules comprise growth factors.

* * * * *